United States Patent
Yang

(10) Patent No.: US 12,226,337 B2
(45) Date of Patent: Feb. 18, 2025

(54) BODY FLUID COLLECTION DEVICE

(71) Applicant: Kuohuang Yang, Taipei (TW)

(72) Inventor: Kuohuang Yang, Taipei (TW)

( * ) Notice: Subject to any disclaimer, the term of this patent is extended or adjusted under 35 U.S.C. 154(b) by 641 days.

(21) Appl. No.: 17/255,706

(22) PCT Filed: Jun. 20, 2019

(86) PCT No.: PCT/CN2019/000129
§ 371 (c)(1),
(2) Date: Dec. 23, 2020

(87) PCT Pub. No.: WO2020/000994
PCT Pub. Date: Jan. 2, 2020

(65) Prior Publication Data
US 2021/0282960 A1  Sep. 16, 2021

(30) Foreign Application Priority Data

Jun. 26, 2018 (CN) .......................... 201820986228.6

(51) Int. Cl.
  *A61F 5/44* (2006.01)
  *A61F 5/443* (2006.01)
  *A61F 5/453* (2006.01)

(52) U.S. Cl.
  CPC ............ *A61F 5/4404* (2013.01); *A61F 5/443* (2013.01); *A61F 5/453* (2013.01)

(58) Field of Classification Search
  CPC ........ A61F 5/4404; A61F 5/443; A61F 5/453; A61F 5/4407; A61F 5/445; A61F 5/448; A61F 5/455; A61F 5/44; A61F 5/4408
  See application file for complete search history.

(56) References Cited

U.S. PATENT DOCUMENTS 3,897,785 A * 8/1975 Barto, Jr. ............... A61F 5/4408
 604/327
4,211,224 A * 7/1980 Kubach ................... A61F 5/441
 604/333

(Continued)

FOREIGN PATENT DOCUMENTS

CN  1233945 A  11/1999
CN  203017152 U  6/2013

(Continued)

OTHER PUBLICATIONS

International Search Report in PCT/CN2019/000129 dated Sep. 26, 2019, 6 pages (with English translation).

*Primary Examiner* — Ariana Zimbouski
(74) *Attorney, Agent, or Firm* — CANTOR COLBURN LLP

(57) ABSTRACT

A body fluid collection device (10), comprising: a first sheet (11) that is provided with a first opening (12) and that comprises a first surface (S1) and a second surface (S2), the first surface (S1) being provided with an adhesive layer (13); a second sheet (21) that is provided with a second opening (22) and that comprises a third surface (S3) and a fourth surface (S4), the third surface (S3) and the second surface (S2) being interconnected with a first closed strip-shaped region (1121); a third sheet (31) that comprises a fifth surface (S5) and a sixth surface (S6), the second sheet (21) and the third sheet (31) being interconnected with a second closed strip-shaped region (2131) so as to form a bag body. The body fluid collection device may be used for collecting different body fluids, thus solving problems such as milk leakage and urine leakage for a user.

14 Claims, 11 Drawing Sheets

(56) References Cited

U.S. PATENT DOCUMENTS

| | | | | |
|---|---|---|---|---|
| 4,238,059 A * | 12/1980 | Caraway | | A61F 5/4405 |
| | | | | 285/332 |
| 4,300,560 A * | 11/1981 | Steer | | A61F 5/445 |
| | | | | 222/530 |
| 4,604,095 A * | 8/1986 | Samuelsen | | A61F 5/4405 |
| | | | | 604/350 |
| 4,681,574 A * | 7/1987 | Eastman | | A61F 5/443 |
| | | | | 604/344 |
| 4,917,689 A * | 4/1990 | Coombes | | A61F 5/445 |
| | | | | 604/338 |
| 5,234,420 A * | 8/1993 | Horton | | A61F 5/4408 |
| | | | | 224/663 |
| 5,409,474 A * | 4/1995 | Fleeman-Hardwick | | |
| | | | | A61F 5/44 |
| | | | | 600/580 |
| 5,437,622 A * | 8/1995 | Carion | | A61F 13/023 |
| | | | | 128/853 |
| 5,458,114 A * | 8/1995 | Herr | | A61F 6/02 |
| | | | | 128/842 |
| 8,551,062 B2 * | 10/2013 | Kay | | A61F 5/453 |
| | | | | 604/257 |
| 8,690,849 B2 * | 4/2014 | Bach | | A61F 5/443 |
| | | | | 604/344 |
| 10,105,255 B2 * | 10/2018 | Fattman | | A61F 5/448 |
| 2005/0177119 A1 * | 8/2005 | Tsai | | A61F 5/445 |
| | | | | 604/332 |
| 2014/0128826 A1 * | 5/2014 | Klein | | A61F 5/443 |
| | | | | 604/344 |
| 2014/0276494 A1 * | 9/2014 | Cisko | | A61M 1/602 |
| | | | | 604/327 |

FOREIGN PATENT DOCUMENTS

| | | |
|---|---|---|
| CN | 104755249 A | 7/2015 |
| CN | 106659581 A | 5/2017 |
| CN | 107874790 A | 4/2018 |
| JP | H09313517 A * | 12/1997 |

* cited by examiner

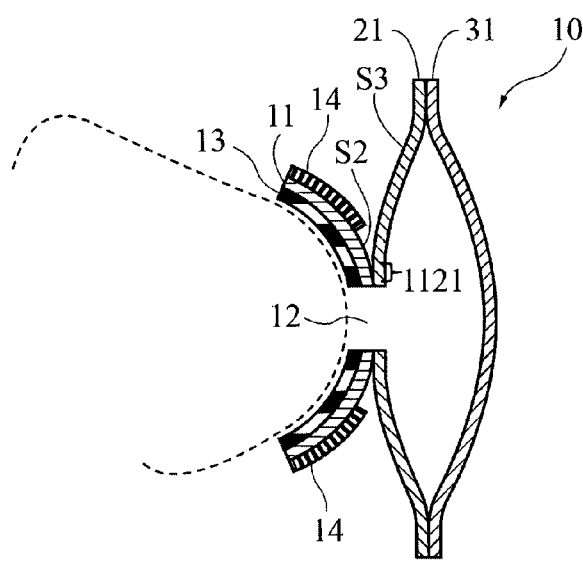
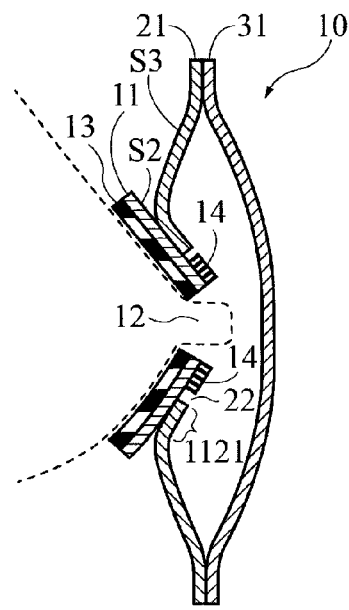
FIG. 5B
FIG. 5C
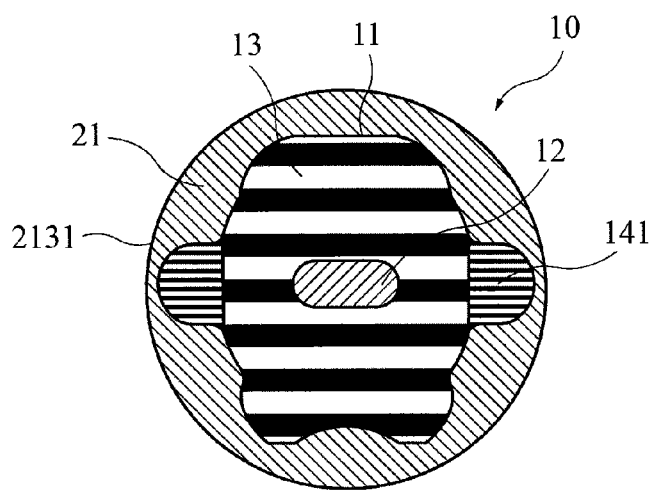
FIG. 5D

BODY FLUID COLLECTION DEVICE

CROSS REFERENCE TO RELATED APPLICATION

This application is a 35 U.S.C. 371 National Phase Entry Application from PCT/CN2019/000129, filed Jun. 20, 2019, which claims priority to Chinese Patent Application No. 201820986228.6, filed Jun. 26, 2018, the disclosures of which are incorporated herein in their entirety by reference, and priority is claimed to each of the foregoing.

BACKGROUND

Technical Field

The present invention relates to a body fluid collection device, and more particularly to a collection device for collecting milk, urine or semen.

Related Art

It is difficult to timely collect body fluids which cannot be controlled, such as breast milk of nursing mothers, urine of infants and young children for testing, urine of urinary incontinence patients, and semen collected for reproductive testing. Such collection procedures often result in pollution to clothes and bedding as well as embarrassment of clients and collectors.

Although there have been several solutions for the collection of such body fluids in the prior art, such as milk collection covers, urine bags connected with catheters of various diameters, stickup urine collection bags for babies, or condoms, these prior art fluid collection devices still have many shortcomings. For example, nursing mothers have to constantly change the anti-galactorrhea pad, urinary incontinence patients have to constantly change thick diapers or carry an indwelling urinary catheter to guide urine to a urine bag, and semen to be collected needs to be accurately injected into a small container.

Because these prior art body fluid collection devices are designed to be able to be repeatedly adhered/removed, the adhesive strength may decrease after being used. As a result, after receiving an amount of body fluid, the body fluid collection device may fall off due to insufficient adhesive strength. This is a problem to be solved in the prior art.

In addition, another problem commonly seen in the prior art is that the position to be adhered is not always a continuous flat surface, for example, female breasts or male and female external genitals are not continuous flat surfaces, and during adhesion, the adhesive part of the body fluid collection device does not fit the body surface and may deform, and movement of the user may also affects the firmness of adhesion. Therefore, how to make the body fluid collection device easily fit the curved body surface and adapt to movement of the user is also a problem to be solved in the prior art.

In addition, another problem commonly seen in the prior art is that in use, the body fluid infiltrates into the adhesive part of the body fluid collection device, leading to a decreased adhesive strength and falling of the device. Therefore, how to improve the prior art so that the collected body fluid does not easily infiltrate into the adhesive site is also a problem to be solved.

SUMMARY

In view of the above problems, the present invention provides a body fluid collection device, which is easy to adhere to the human body and does not easily peel off, and is capable of collecting various body fluids such as milk, urine or semen while preventing leakage which may lead to contamination.

To achieve the above objectives, the present invention provides a body fluid collection device, including: a first sheet, including a first surface and a second surface, and provided with a first opening running through the first sheet, the first surface being provided with an adhesive layer; a second sheet, including a third surface and a fourth surface, and provided with a second opening running through the second sheet, the third surface and the second surface being interconnected with a first closed strip-shaped region; a third sheet, including a fifth surface and a sixth surface, the second sheet being connected to the third sheet with a second closed strip-shaped region, so as to form a bag body.

To achieve the above objectives, the present invention provides a body fluid collection device, including: a first sheet, including a first surface, and provided with a first opening running through the first sheet, the first surface being provided with an adhesive layer; a second sheet, provided with a second opening running through the second sheet, an edge of the second opening being connected in an enclosed manner to an edge of the first opening in the form of a continuous material; a third sheet, connected in an enclosed manner to an edge of the second sheet in the form of a continuous material, so as to form a bag body.

Preferably, in the body fluid collection device, the edge of the first opening, the edge of the second opening and an inner edge of the first closed strip-shaped region coincide with each other.

Preferably, in the body fluid collection device, the first opening is smaller than the second opening, and the edge of the second opening and the inner edge of the first closed strip-shaped region coincide with each other.

Preferably, in the body fluid collection device, the first opening is smaller than the second opening, and the edge of the second opening is located between the first opening and the inner edge of the first closed strip-shaped region or coincide with the first opening, and the edge of the first opening is separated from the edge of the second opening.

The present invention is applicable to the collection of different body fluids, such as milk, semen, blood, menstrual blood, pleural effusion, ascites, interstitial fluid, or urine.

The present invention is a body fluid collection device that can hold different amounts of body fluid, and can be used in combination with sheets of different materials, shapes or sizes to fabricate bags of different volumes or shapes. For example, when the present invention is used as a semen collection device, the second sheet and the third sheet having a small perimeter and thickness can make the body fluid collection device small and thin, to increase pleasure during a sexual life process. The volume is set with reference to an average amount of sperm per ejaculate by male.

In the present invention, considering the convenience of material processing, the body fluid collection device may be designed to be formed by separated sheets connected to each other or made of a continuous material.

The present invention may have various additional designs depending on different purposes of collecting body fluids or different occasions of use.

Main beneficial effects of the present invention: The body fluid collection device of the present invention has a simple structure, is easy to adhere to the human body, and can effectively prevent the leakage of body fluids collected.

Main beneficial effects of the present invention: With the design that the third surface and the second surface are interconnected with the first closed strip-shaped region, the force received by the first sheet is concentrated at the first closed strip-shaped region with firm connection, so that the body fluid collection device of the present invention will not peel off from the human body due to friction, pulling, hydraulic pressure or pressure in use.

Main beneficial effects of the present invention: The edge of the first sheet is separated from the edge of the second sheet, and an effect of fixing both the inner side and the outer side of the first sheet by using the adhesive layer is produced when using the outer edge of the first closed strip-shaped region as a reference point, thereby effectively resisting the peeling of the first sheet from the body surface due to pulling by the second sheet or the gravity of the bag body. The first sheet and the second sheet may be made of an elastic material to better buffer the acting force.

Main beneficial effects of the present invention: As the first sheet has a small thickness, its edge does not easily warp or peel off due to friction. In addition, the first sheet has good air permeability and good water permeability which can reduce discomfort and the possibility of skin allergy, and can be repeatedly adhered/removed without causing skin injuries.

Main beneficial effects of the present invention: With the design that the edge of the first sheet is provided with at least one notch, the design of the arc-shaped notch or the design of a petal-shaped edge, the present invention can well fit a non-planar body surface, and can well resist the pulling by an external force when the bag body is filled with a body fluid.

Main beneficial effects of the present invention: By adjusting the relationship between the sizes of the first opening and the second opening and the position at which the first closed strip-shaped region is disposed, the hydraulic pressure will be guided to the inner edge of the first closed strip-shaped region the bag body is filled with the body fluid, thereby reducing the possibility that the body fluid leaks out from the edge of the first opening.

Main beneficial effects of the present invention: The structure maintaining unit extending along the edge of the first sheet or the edge of the first opening prevents the formation of wrinkles at the edge of the first sheet to cause the body fluid to leak from the wrinkles.

Main beneficial effects of the present invention: The second sheet and the third sheet are each a rounded rectangle having a long symmetry axis and a short symmetry axis. A ratio of the long symmetry axis to the short symmetry axis is greater than or equal to 2:1. The elongated belt-shaped bag body, when fixed to the user's leg, allows for even distribution of the weight of urine to ensure a stable center of gravity and that the user can freely move his/her legs.

Main beneficial effects of the present invention: An embodiment of the body fluid collection device may be used as a milk collection device, a urine bag, or a semen collection device for contraception. By means of these implementations, the present invention can solve the problems of milk leakage, urine leakage, semen test or even contamination by nocturnal emission.

BRIEF DESCRIPTION OF THE DRAWINGS

FIG. 5A to FIG. 5D are schematic diagrams of showing a method of use and effects of the body fluid collection device;

DETAILED DESCRIPTION

Figure 1:
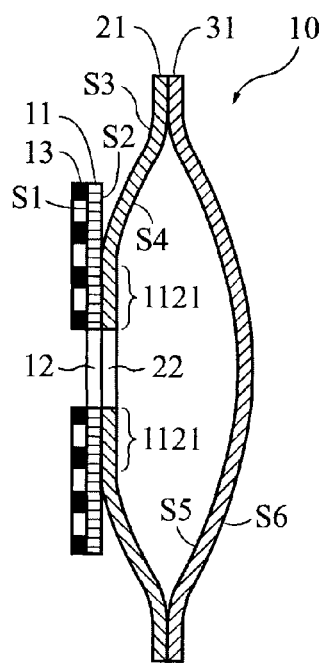
FIG. 1 is a schematic diagram of a body fluid collection device according to the present invention.

Specific implementations of the present invention are described below with reference to the accompanying drawings, where same or similar parts are denoted by same reference numerals.

A body fluid collection device 10 shown in FIG. 1 is an embodiment of the present invention. The body fluid collection device 10 includes: a first sheet 11 that is provided with a first opening 12 and that includes a first surface S1 and a second surface S2, the first surface S1 being provided with an adhesive layer 13 for adhesion to a user; a second sheet 21 that is provided with a second opening 22 and that includes a third surface S3 and a fourth surface S4, the third surface S3 being connected to the second surface S2 of the first sheet 11 along a circle, ellipse, or rounded regular polygon with a first closed strip-shaped region 1121, an outer edge of the first closed strip-shaped region 1121 being located between an edge of the first sheet 11 and the first opening 12; and a third sheet 31 that includes a fifth surface S5 and a sixth surface S6, an edge of the third sheet 31 being connected to the second sheet 21 in an enclosed manner so as to form a bag body having an opening, for storing a body fluid.

Figures 2A, 2B, 2C:
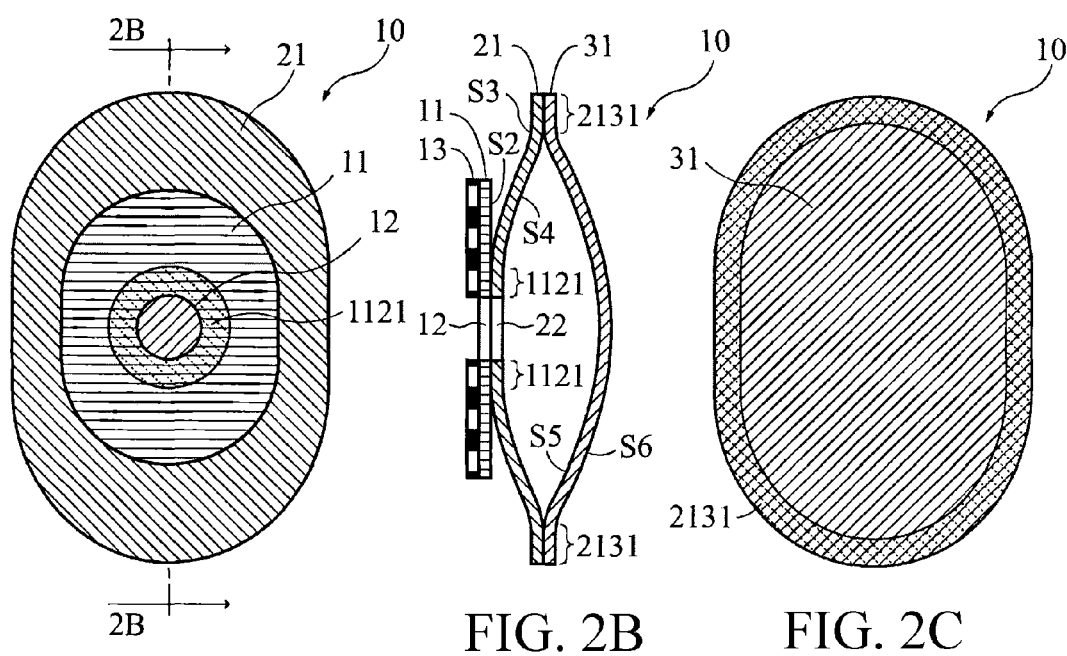
FIG. 2A to FIG. 2C are schematic diagrams of the body fluid collection device from different viewing angles.

FIG. 2A to FIG. 2C are schematic diagrams of the body fluid collection device 10 from different viewing angles, where FIG. 2A is a front view (in which the adhesive layer 13 is not shown), FIG. 2B is a cross-sectional view, and FIG. 2C is a rear view. As shown in FIG. 2B (FIG. 2B is a vertical cross-section of FIG. 2A), the fifth surface S5 of the third sheet 31 and the fourth surface S4 of the second sheet 21 are connected with a second closed strip-shaped region 2131 (as shown in FIG. 2B and FIG. 2C). In this embodiment, an edge of the first opening 12, an edge of the second opening 22 and an inner edge of the first closed strip-shaped region 1121 coincide with each other and form the opening of the bag body (as shown in FIG. 2B). The opening may be, but not limited to, circular or elliptical. The first sheet 11, the second sheet 21, and the third sheet 31 may each be fabricated as a flat or arc-surface film, and may be in the shape of, but not limited to, a circle, ellipse, or rounded regular polygon.

The body fluid collection device 10 may be made of, for example, but not limited to, natural latex, synthetic latex, rubber, silicone, polyisoprene (PI), polyurethane (PU), polyethylene (PE), a polymer material, a biomaterial or a synthetic DNA material. The material constituting the adhesive layer 13 may include, for example, a pressure-sensitive adhesive. The first sheet 11 may be made of a viscous material. The third surface S3 of the second sheet 21 and the second surface S2 of the first sheet 11 are interconnected, and the fifth surface S5 of the third sheet 31 and the fourth surface S4 of the second sheet 21 are interconnected. The interconnection may be achieved by using, for example, but not limited to, a solvent, an adhesive, a tape, or a glue film, or may be achieved by, for example, but not limited to, electric, ultrasonic, or high-frequency welding.

Figure 3A:
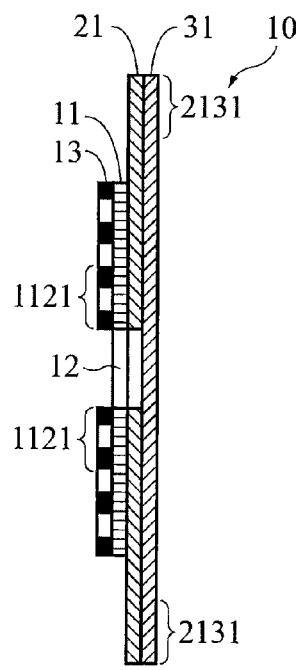
FIG. 3A and FIG. 3B are schematic diagrams of another embodiment of the body fluid collection device.
Figure 3B:
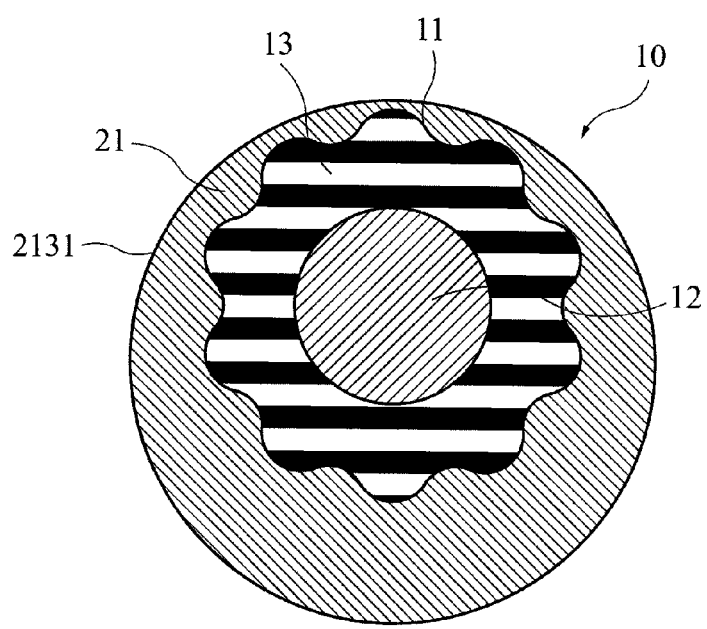

To resist friction, pulling, hydraulic pressure, or gravity and prevent the device of the present invention from detaching from the human body to lead to body fluid leakage, as shown in FIG. 3A, the first sheet 11, the second sheet 21, and the third sheet 31 may each be a soft sheet which is flat in natural state, is preferably, but not necessarily, made of an elastic material, and preferably has a thickness of no more than 0.1 mm. The first sheet 11 which is configured for adhesion to the user's skin requires good air permeability and may be made of a microporous film (for example, but not limited to, a highly air/water-permeable PU film) having a thickness of, for example, less than 0.1 mm, preferably less than 0.05 mm, more preferably less than 0.03 mm; the air permeability thereof is preferably a moisture vapor transmission rate (MVTR) of greater than or equal to 500 g/(m$^2$·24 h), and the water permeability after gluing thereof is preferably greater than or equal to 1000 g/(m$^2$·24 h). A smaller thickness of the first sheet 11 leads to better fitness and that the edge of the first sheet is less prone to warpage or peeling caused by friction. A higher air/water permeability of the first sheet 11 leads to less discomfort caused by long-time use and a smaller possibility of skin allergy. As shown in FIG. 3B, the second sheet 21 and the third sheet 31 are interconnected with their respective edges. In this case, the second closed strip-shaped region 2131 is a closed line having a substantial width. The edge of the first sheet 11 may be provided with at least one notch, preferably, for example, an arc-shaped notch. When the body fluid collection device 10 is adhered to a curved body surface, the notch can prevent from formation of raised wrinkles at the edge of the first sheet 11, thereby improving the tightness of adhesion. Alternatively, the first sheet 11 may have a petal-shaped edge, and therefore can well fit a non-planar surface. In addition, the first sheet 11 having a petal-shaped edge may provide a claw-like grip, which can well resist the pulling of an external force when the bag body is filled with a body fluid.

Figure 4A:
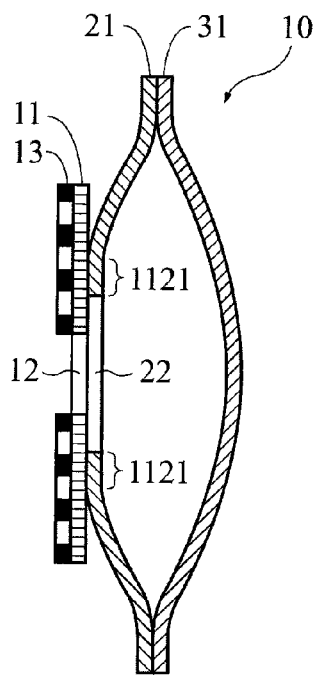
FIG. 4A to FIG. 4C are schematic diagrams of different aspects of the opening of the bag body of the body fluid collection device.
Figure 4B:
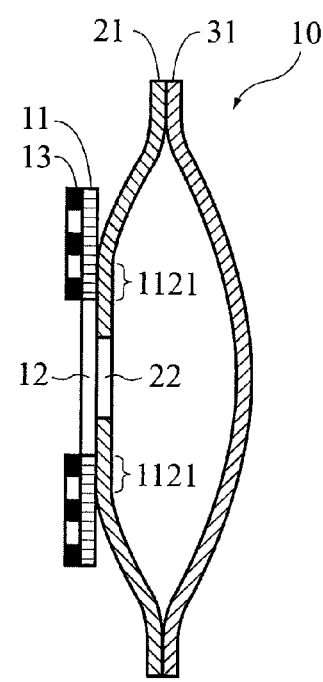
Figure 4C:
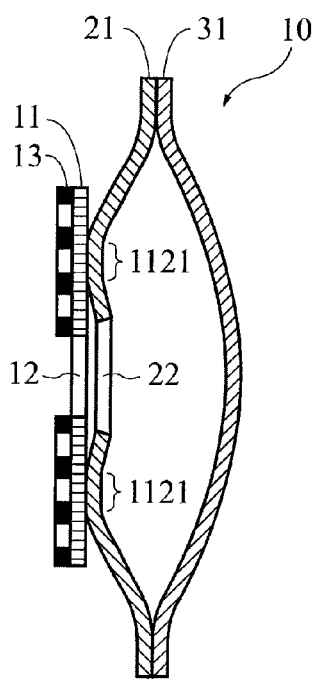

FIG. 4A to FIG. 4C are schematic diagrams of different aspects of the opening of the bag body when the body fluid collection device 10 is used for different purposes. As shown in FIG. 4A, the first opening 12 is smaller than the second opening 22, and the edge of the second opening 22 coincides with the inner edge of the first closed strip-shaped region 1121, so that the opening of the bag body is the first opening 12. As shown in FIG. 4B, the first opening 12 is larger than the second opening 22, and the edge of the first opening 12 coincides with the inner edge of the first closed strip-shaped region 1121, so that the opening of the bag body is the second opening 22. As shown in FIG. 4C, the first opening 12 is smaller than the second opening 22, the edge of the second opening 22 is located between the first opening 12 and the inner edge of the first closed strip-shaped region 1121, and the edge of the second opening 22 in the bag body is not connected to the first sheet 11, so that the opening of the bag body is the first opening 12. The edge of the opening of the bag body shown in FIG. 4A and FIG. 4C has only one layer, i.e., the first sheet 11, which, if having a thickness of less than 0.1 mm, can more effectively preventing the body fluid from leaking from the edge of the first opening 12. In addition, as shown in FIG. 4C, when the bag body is filled with the body fluid, the hydraulic pressure will be guided to the inner edge of the first closed strip-shaped region 1121 with which the first sheet 11 and the second sheet 21 are connected, thereby reducing the possibility that the body fluid leaks out from the edge of the first opening 12. Moreover, in these embodiments, an effect of fixing both the inner side and the outer side of the first sheet 11 by using the adhesive layer 13 is produced, when using the outer edge of the first closed strip-shaped region 1121 as a reference point, thereby effectively resisting the peeling of the first sheet 11 from the body surface due to pulling by the second sheet 21 or the gravity of the bag body.

Figure 5A:
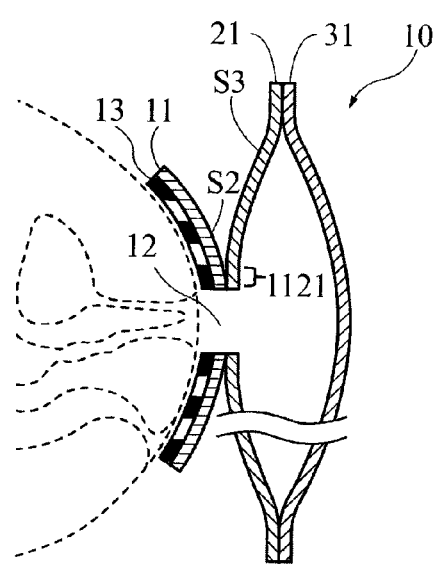

FIG. 5A to FIG. 5D are schematic diagrams illustrating different methods of using the body fluid collection device 10, where FIG. 5A is used for collecting urine or menstrual blood of a female, FIG. 5B is used for collecting urine or semen of a male, and FIG. 5C is used for collecting milk of a female. In these embodiments, the outer edge of the first closed strip-shaped region 1121 is smaller than the edge of the first sheet 11 and is smaller than the edge of the second sheet 21. The second surface S2 adjacent to the edge of the first sheet 11 is away from the third surface S3 of the second sheet 21 (the part of the second surface S2 adjacent to the edge is separated from the third surface S3), so that an acting force generated on the first sheet 11 due to pulling of the second sheet 21 (or hydraulic pressure or gravity) can be mitigated, making the first sheet 11 not easily peel off from the human body. The first sheet 11 and the second sheet 21 may be made of an elastic material to better mitigate the acting force. As shown in FIG. 5A, in use, the opening of the bag body is aligned with the urethra orifice and ostium vaginae of a female user, and the first sheet 11 is adhered to the vulva by means of the adhesive layer 13, so that urine or menstrual blood can flow into the bag body. As shown in FIG. 5B, in use, the opening of the bag body is aligned with the urinary meatus of a male user, and the first sheet 11 is adhered to the balanus or penis by means of the adhesive layer 13, so that urine or semen can flow into the bag body.

in these embodiments, the body fluid collection device 10 may further include a structure support unit 14, which extends along the second surface S2 at the edge of the first sheet 11 (as shown in FIG. 5B), and functions as a frame disposed on the first sheet 11, to maintain the shape of the edge of the first sheet 11 before adhesion, thereby preventing from formation of wrinkles during the adhesion of the first sheet 11 to the user. After adhesion, the user may remove the structure support unit 14 by adjusting the adhesiveness (for example, by making the adhesiveness between the structure support unit 14 and the first sheet 11 weaker than the adhesiveness between the first sheet 11 and the human body through the adhesive layer 13). As shown in FIG. 5C, the first opening 12 is smaller than the second opening 22, and the edge of the second opening 22 coincides with the inner edge of the first closed strip-shaped region 1121 (also referring to FIG. 4A). In use, the first opening 12 is aligned with a nipple of a female user, and the first sheet 11 is adhered to the breast through the adhesive layer 13, so that milk can flow into the bag body. When the first sheet 11 is adhered to a curved body surface, the edge of the first opening 12 is prone to wrinkles, through which the body fluid may leak out from the edge of the first sheet 11. In view of this problem, a structure support unit 14 surrounding the edge of the first opening 12 may further be disposed on the second surface S2 of the first sheet 11, to maintain the shape of the first opening 12, thereby preventing from formation of wrinkles at the first opening 12 to lead to leakage. As shown in FIG. 5D (where the body fluid collection device 10 is adhered to balanus), the structure support unit 14 may extend from the edge to form a pinch portion 141, with at least one point being connected to the structure support unit 14, for the user to pinch with fingers to adjust the position of the body fluid collection device 10 before adhesion or remove the structure support unit 14 after adhesion. In addition, the penis surface at the junction of the frenulum of prepuce and the coronal sulcus adjacent to the scrotum is uneven, is the part that has the strongest friction during a sexual life process, and is also a part to which a bottom edge of the first sheet 11 is adhered. In an embodiment where the present invention is used for contraception, the bottom edge of the first sheet 11 may further be provided with an arc-shaped notch, to make the first sheet 11 less easily peel off from the bottom edge.

When the present invention is used as a semen collection device, the second sheet 21 (or the third sheet 31) has a perimeter of, for example, less than 180 mm, preferably less than 150 mm, and more preferably less than 120 mm, and a thickness of, for example, less than 0.1 mm, preferably less than 0.05 mm, and more preferably less than 0.03 mm, and the bag body has a volume of, for example, less than 20 mL, preferably less than 15 mL, and more preferably less than 10 mL. The small perimeter and thickness make the body fluid collection device 10 small and thin, so as to increase pleasure during a sexual activity process. The volume is set with reference to the fact that the amount of sperm per ejaculate by male is generally no more than 10 mL.

Figure 6A:
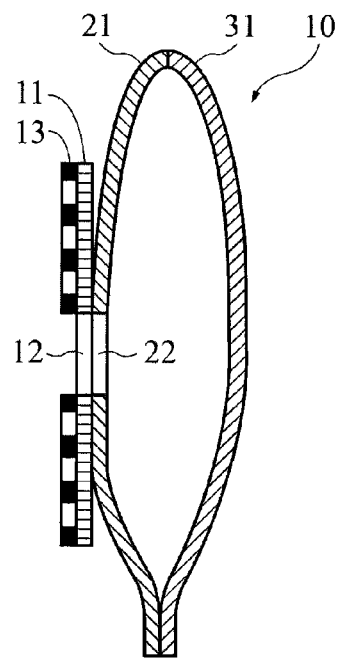
FIG. 6A and FIG. 6B are schematic diagrams of another embodiment of the body fluid collection device.
Figure 6B:
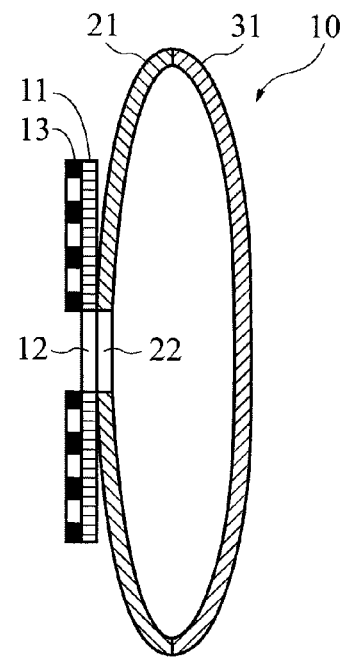

FIG. 6A and FIG. 6B show another embodiment of the present invention. At least part of the edge of the third sheet 31 and at least part of the edge of the second sheet 21 of the body fluid collection device 10 are connected in the form of a continuous material during manufacturing. As shown in FIG. 6A, in a method for connecting the third sheet 31 and the second sheet 21 in the form of a continuous material, for example, a sheet having the second opening 22 is folded to define two sheet parts, where the part with the second opening 22 is equivalent to the second sheet 21, and the part without the second opening 22 is equivalent to the third sheet 31; then other open edges are connected, thus forming the structure as shown in FIG. 6A. As shown in FIG. 6B, the edge of the third sheet 31 and the edge of the second sheet 21 are connected in the form of a continuous material, and may be fabricated by, for example, but not limited to, blow molding, 3D printing, or dip forming.

Figure 7:
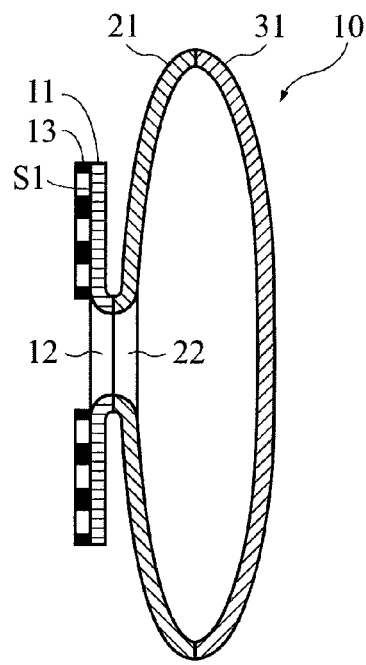
FIG. 7 is a schematic diagram of another embodiment of the body fluid collection device according to the present invention.

FIG. 7 shows a body fluid collection device 10 according to an embodiment of the present invention. The body fluid collection device 10 includes: a first sheet 11 that is provided with a first opening 12 and that includes a first surface S1, the first surface S1 being provided with an adhesive layer 13 for adhesion to a user; a second sheet 21 that is provided with a second opening 22, an edge of the second opening 22 being connected in an enclosed manner to the edge of the first opening 12 of the first sheet 11 along a circle, ellipse, or rounded regular polygon in the form of a continuous material; and a third sheet 31, having an edge connected in an enclosed manner to the edge of the second sheet 21 in the form of a continuous material, so as to form a bag body having an opening to store a body fluid. In this embodiment, the connection between the edge of the third sheet 31 and the edge of the second sheet 21 or the connection between the edge of the second sheet 21 of the second opening 22 and the edge of the first opening 12 of the first sheet 11 may be achieved by, for example, but not limited to, blow molding, 3D printing, or dip forming.

Figure 8A:
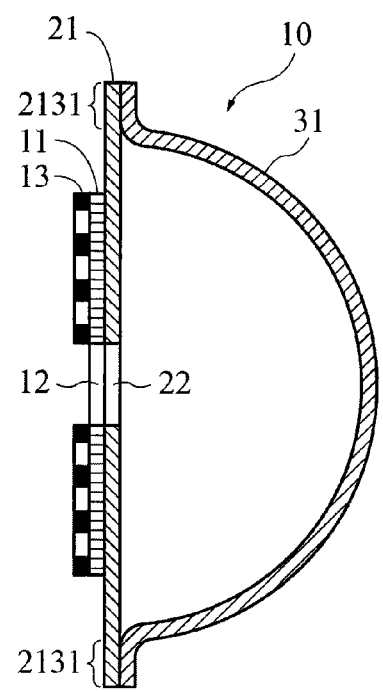
FIG. 8A and FIG. 8B are schematic diagrams of another embodiment of the body fluid collection device.
Figure 8B:
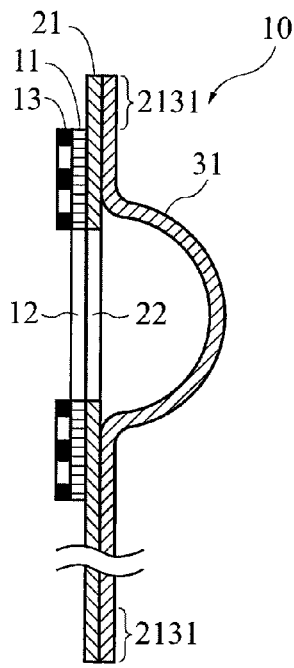
Figure 9:
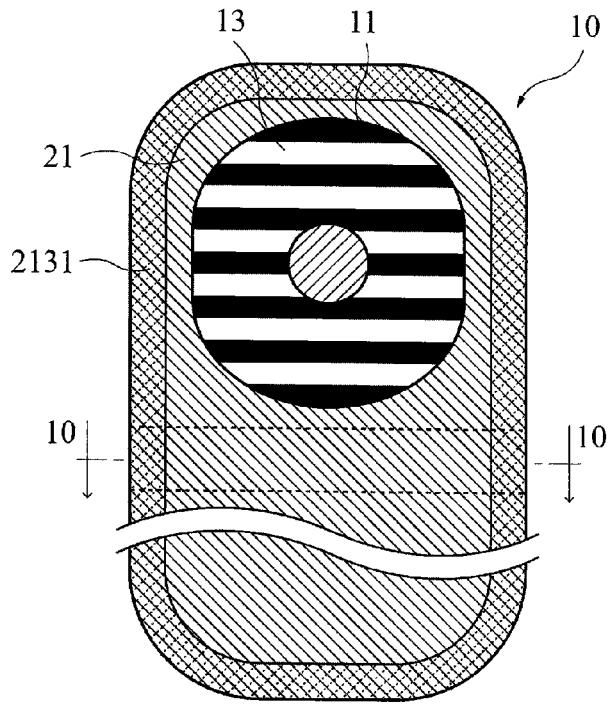
FIG. 9 is a schematic diagram of another embodiment of the body fluid collection device according to the present invention.

FIG. 8A and FIG. 8B show another embodiment of the present invention. The third sheet 31 of the body fluid collection device 10 may be a flat sheet, an arc-surface sheet or a combination thereof in natural state. As shown in FIG. 8A, the third sheet 31 is fabricated as an arc-surface film to increase the volume of the bag body to collect more body fluid. As shown in FIG. 8B, the third sheet 31 is a soft sheet which is partially flat and partially arc-surface, where parts of the third sheet 31 adjacent to the edge are fabricated as flat structures and the middle part is fabricated as an arc-surface structure (or cystic structure). A large opening of the bag body allows at least part of a human organ (for example, but not limited to, nipple or an infant's penis) to pass through and be accommodated in the space inside the bag body. The arc-surface structure may be fabricated by, for example, but not limited to, vacuum forming, air-pressure molding, matched-die molding, blow molding, 3D printing, or dip forming.

Figure 10A:
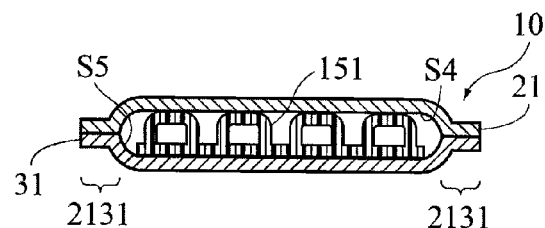
FIG. 10A to FIG. 10C are schematic diagrams showing that the body fluid collection device includes a spacer.
Figure 10B:
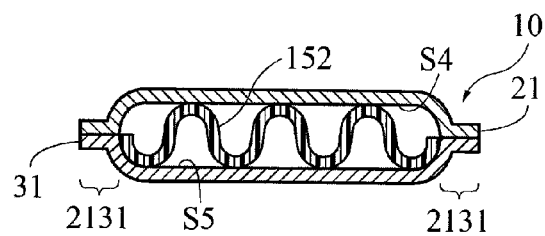
Figure 10C:
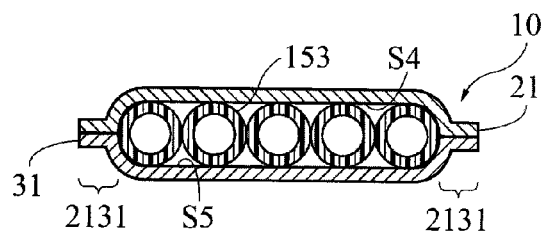

As shown in FIG. 9 and FIG. 10A to FIG. 10C, a spacer may further be disposed between the fourth surface S4 of the second sheet 21 and the fifth surface S5 of the third sheet 31 of the body fluid collection device 10. FIG. 10A to FIG. 10C show horizontal cross-sections of FIG. 9. Due to the presence of the spacer, the fourth surface S4 of the second sheet 21 and the fifth surface S5 of the third sheet 31 do not come into fully contact with each other and do not form a closed space inside the bag body. The spacer has a three-dimensional structure and may include, but not limited to, at least one of the following components: a bubble wrap 151 (as shown in FIG. 10A), a corrugated board 152 (as shown in FIG. 10B), and one or more tubular elements 153 (as shown in FIG. 10C). The body fluid flows along a gap formed between the second sheet 21, the third sheet 31 and the spacer, thereby effectively preventing the flow of the body fluid from being blocked due to the compression of the bag body by limbs or clothes.

Figure 11A:
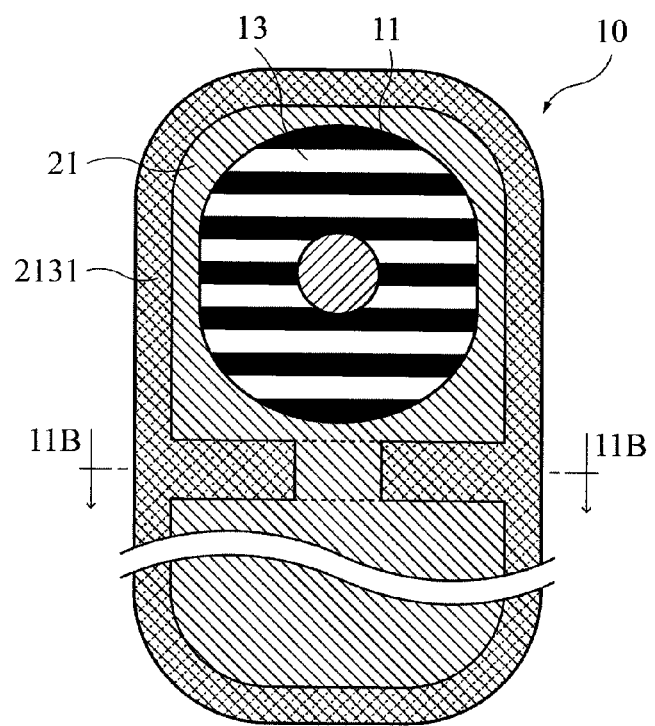
FIG. 11A and FIG. 11B are schematic diagrams showing that the body fluid collection device includes a unidirectional element.
Figure 11B:
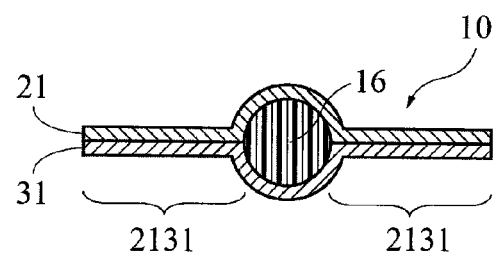

FIG. 11A shows another embodiment of the body fluid collection device 10 of the present invention. FIG. 11B shows a horizontal cross-section of FIG. 11A. The fourth surface S4 of the second sheet 21 is partially connected to the fifth surface S5 of the third sheet 31, dividing the bag body into two spaces which are in communication with each other through a passage (as shown in FIG. 11A). A spacer may further be disposed in the passage so that the two spaces of the bag body are in communication with each other through the spacer. The spacer is a unidirectional element 16 having a one-way flow guiding function (as shown in FIG. 11B), and may be, but not limited to, a one-way valve or a flow meter. The one-way valve is configured to prevent backflow of urine (which easily leads to urinary tract infection). The flow meter is configured to measure the volume of urine flow of the user.

Figure 12A:
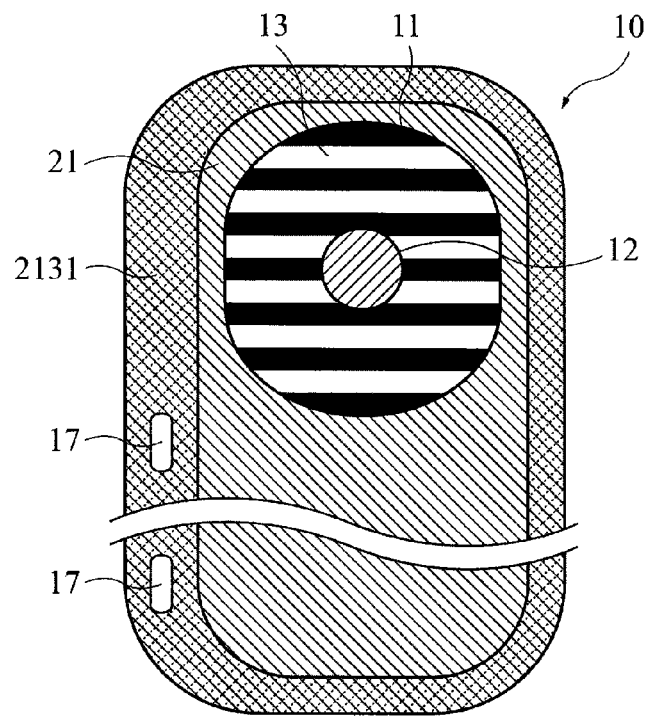
FIG. 12A and FIG. 12B are schematic diagrams showing that the body fluid collection device is provided with a rope hole.
Figure 12B:
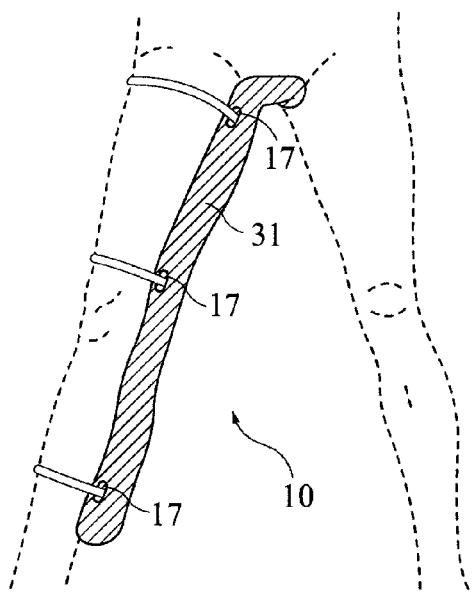

FIG. 12A shows an embodiment of the present invention. The second sheet 21 and the third sheet 31 are each a rounded rectangle having a long symmetry axis and a short symmetry axis. The opening of the bag body is provided adjacent to an end of the long symmetry axis. At least one rope hole 17 is formed within the second closed strip-shape region, so that in use, the bag body may be fixed to the user's leg by using a rope, adhesive tape or hook and loop fastener passing through the rope hole 17 (as shown in FIG. 12B), thereby preventing the bag body full of urine from being pulled and reducing sway of the bag body. A ratio of the long symmetry axis to the short symmetry axis may be, for example, greater than 2:1, preferably greater than 3:1, and more preferably greater than 4:1. The elongated belt-shaped bag body also have the advantages of even distribution of the weight of the body fluid to ensure a stable center of gravity and that the user can freely move his/her legs and can sit, stand, lie, or walk without restrictions. It may be understood by those of ordinary skill in the art that the rope hole 17 may also be used as a button hole configured to connect to a button for fixing.

Figure 13:
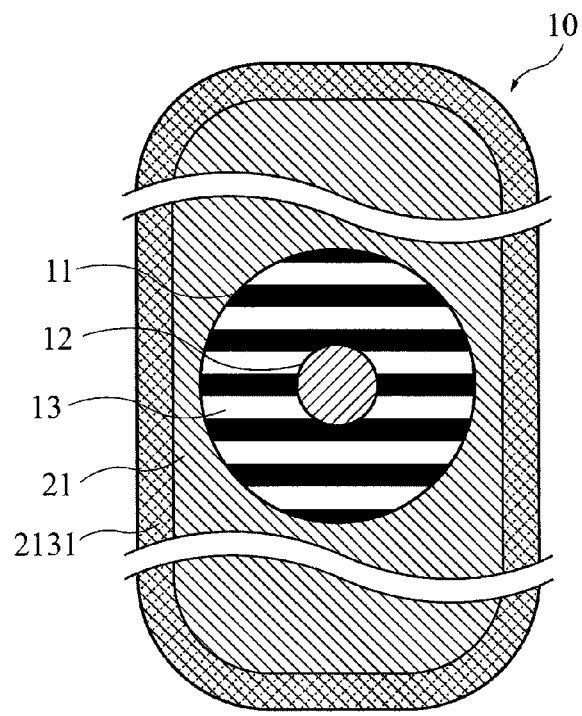
FIG. 13 is a schematic diagram of another embodiment of the body fluid collection device according to the present invention.

FIG. 13 shows another embodiment of the present invention. The second sheet 21 and the third sheet 31 are each a rounded rectangle having a long symmetry axis and a short symmetry axis. The opening of the bag body is provided at the middle point of the long symmetry axis, and two ends of the long symmetry axis extends outward to lengthen the bag body, to increase the volume of the bag body and collect more urine. Further, the two ends of the long symmetry axis of the bag body may be respectively fixed to the left and right legs of the user.

Figure 14A:
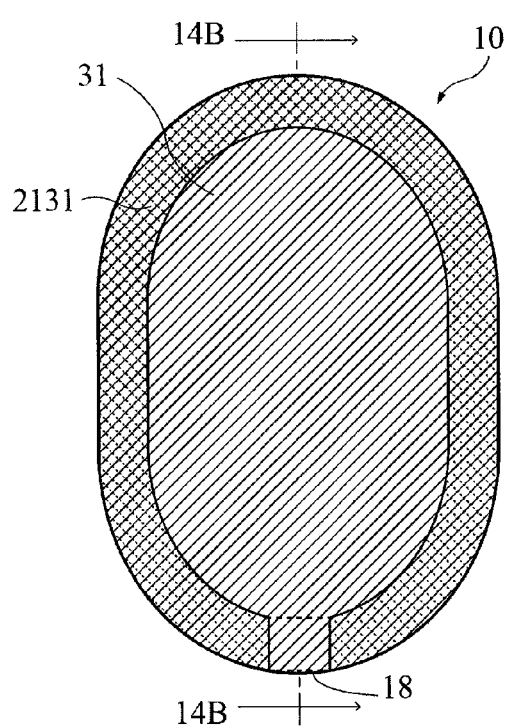
FIG. 14A to FIG. 14C are schematic diagrams showing that the body fluid collection device includes a drainage tube.
Figure 14B:
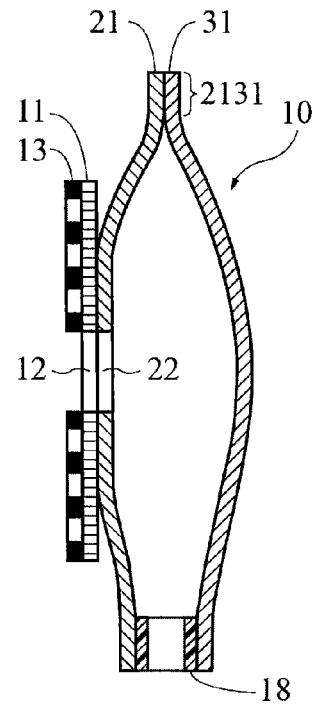
Figure 14C:
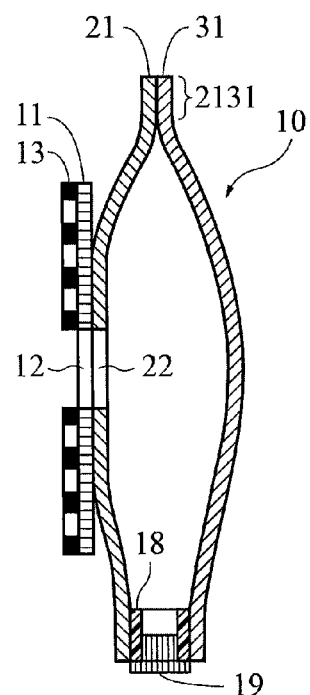

The present invention may further include at least one drainage tube, connected to the second sheet 21 or the third sheet 31 of the bag body, so that the body fluid stored in the bag body may be discharged to the outside of the bag body through the drainage tube. FIG. 14A shows another embodiment of the present invention, and FIG. 14B shows a vertical cross-section of FIG. 14A. The second closed strip-shaped region 2131 of the body fluid collection device 10 has an open part which is not closed. The drainage tube 18 passes through the open part and is then sandwiched between the second sheet 21 and the third sheet 31. The drainage tube 18 is connected to the bag body and may include, but not limited to, at least one of the following components: a cap 19 (as shown in FIG. 14C, the cap 19 is plugged into the drainage tube 18 by means of material elasticity and friction to close the drainage tube 18), a switch, a valve, a flow meter (configured to measure the volume of urine), and a one-way valve (or referred to as a check valve, configured to prevent backflow of urine). The drainage tube 18 shown in FIG. 14B and FIG. 14C is merely an example, and its length may be extended at will.

Figure 15A:
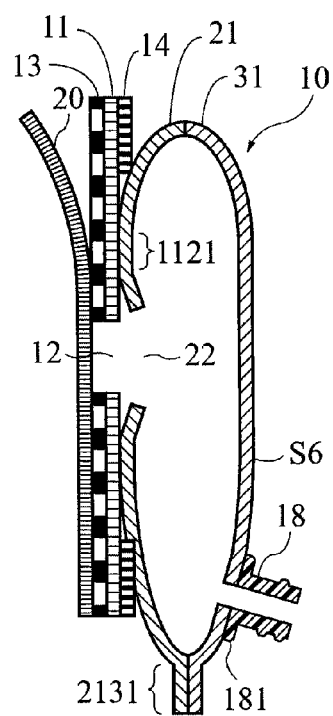
FIG. 15A to FIG. 15E are schematic diagrams of steps of using another embodiment of the body fluid collection device of the present invention.
Figure 15B:
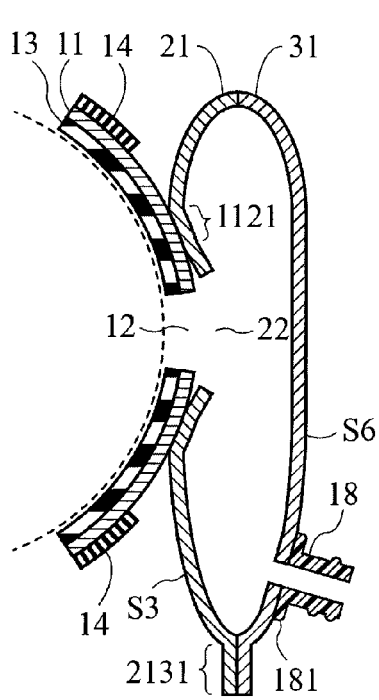
Figure 15C:
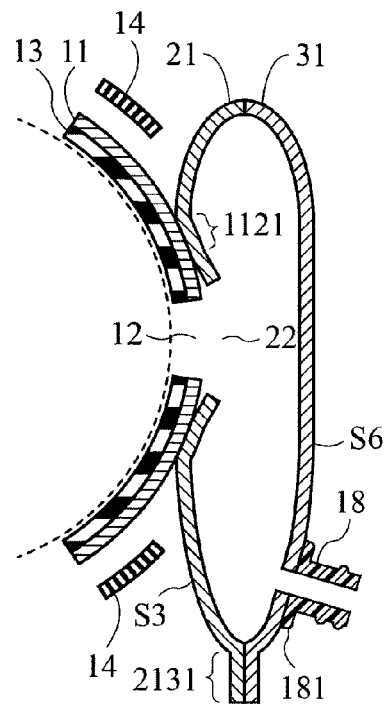
Figure 15D:
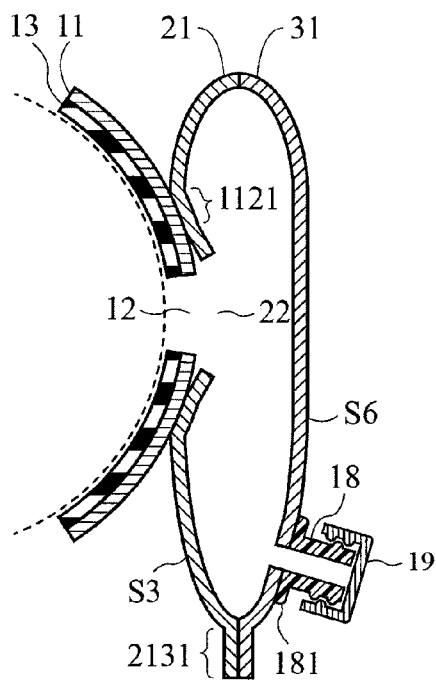
Figure 15E:
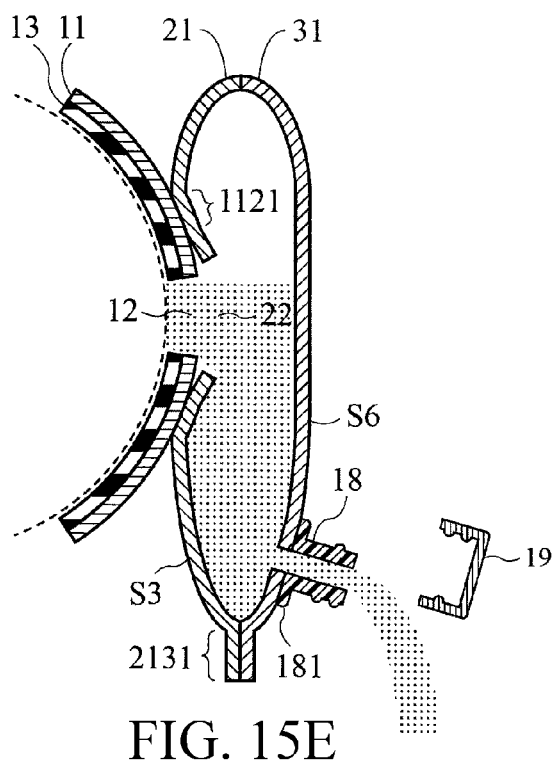

The present invention may further include a release layer 20, which covers at least part of the adhesive layer 13, to prevent the adhesive layer 13 from losing the adhesive property. The release layer 20 may be, for example, a release paper. FIG. 15A to FIG. 15E show steps of collecting milk (urine of a male/female) by using the present invention. The bag body is formed by folding one sheet of continuous material and sealing all or part of its edges. The sealed edges form a second closed strip-shaped region 2131. The first opening 12 is smaller than the second opening 22. The edge of the second opening 22 is located between the first opening 12 and the inner edge of the first closed strip-shaped region 1121 (also referring to FIG. 4C). In step 1, as shown in FIG. 15A, in use, the release layer 20 of the body fluid collection device 10 is separated and peeled off to expose the adhesive layer 13 on the first sheet 11. In step 2, as shown in FIG. 15B, the first opening 12 is aligned with a nipple (urinary meatus) of a female and the first sheet 11 is adhered to the breast skin (balanus of a male/labia majora of a female) through the adhesive layer 13. In step 3 (not a necessary step), as shown in FIG. 15C, the structure support unit 14 is removed. In step 4, as shown in FIG. 15D, the cap 19 and the drainage tube 18 are threadedly engaged with each other to close the drainage tube 18. In step 5, as shown in FIG. 15E, the user's milk (urine) flows through the first opening 12 and the second opening 22 and then into the bag body for storage. Then, after coming to an appropriate place, the user opens the drainage tube 18 to discharge the body fluid. In this embodiment, the second sheet 21 or the third sheet 31 is provided with at least one flow guiding opening, and the drainage tube 18 is disposed corresponding to the flow guiding opening, where one end of the drainage tube 18 is provided with a brim portion 181, which is substantially perpendicular to an axial direction of the drainage tube 18, surrounds a periphery of the drainage tube 18, and is connected to the third surface S3 of the second sheet 21 or the sixth surface S6 of the third sheet 31, thereby increasing the tightness and the reliability of connection between the drainage tube 18 and the second sheet 21 or the third sheet 31. In addition, the drainage tube 18 is provided with male threads and the cap 19 is provided therein with female threads so that the two can be detachably engaged with each other. It may be understood by those of ordinary skill in the art that in this embodiment, the design may be simplified by replacing the threads with a flange provided on one of the cap 19 and the drainage tube 18 and a concave edge provided on the other, so that the two can be engaged with each other.

The above descriptions are only examples, not limitations. Any equivalent modifications or variations made without departing from the spirit and scope of the present invention falls within the scope of the appended claims.

LIST OF REFERENCE NUMERALS 10 body fluid collection device
11 first sheet
12 first opening
S1 first surface
S2 second surface
13 adhesive layer
21 second sheet
22 second opening
S3 third surface
S4 fourth surface
1121 first closed strip-shaped region
31 third sheet
S5 fifth surface
S6 sixth surface
2131 second closed strip-shaped region
14 structure support unit
141 pinch portion
151 bubble wrap
152 corrugated board
153 tubular element
16 unidirectional element
17 rope hole
18 drainage tube
181 brim portion 19 cap
20 release layer

What is claimed is:

1. A body fluid collection device, comprising:
a first sheet, provided with a first opening and comprising a first surface and a second surface;
an adhesive layer, disposed on the first surface of the first sheet;
a second sheet, provided with a second opening and comprising a third surface and a fourth surface, the third surface being connected to the second surface of the first sheet with a first closed strip-shaped region, an outer edge of the first closed strip-shaped region being located between an edge of the first sheet and the first opening; and
a third sheet, provided with a fifth surface and a sixth surface, the fifth surface being connected to the fourth surface of the second sheet with a second closed strip-shaped region, so that an edge of the third sheet is connected to an edge of the second sheet in an enclosed manner so as to form a bag body having an opening;
the first opening is smaller than or equal to the second opening so that the opening of the bag body is the first opening, and the edge of the second opening is located between the first opening and the inner edge of the first closed strip-shaped region or coincide with the first opening and in the bag body, the edge of the second opening is separated from the edge of the first opening;
wherein the first sheet has a thickness of less than 0.1 mm;
a structure support unit, which extends along the edge of the first opening, and is disposed on the second surface of the first sheet, wherein the structure support unit substantially maintains a shape of the first opening, and substantially prevents forming wrinkles at the edge of the first opening; and therefore, a body fluid is prevented from leaking out from the edge of the first sheet through the wrinkles of the edge of the first opening.

2. The body fluid collection device according to claim 1, wherein at least part of the edge of the third sheet and at least part of the edge of the second sheet are connected as a result of using a continuous material during manufacturing.

3. The body fluid collection device according to claim 1, wherein at least one rope hole or button hole is formed within the second closed strip-shaped region.

4. The body fluid collection device according to claim 1, wherein the outer edge of the first closed strip-shaped region is smaller than the edge of the first sheet and is smaller than the edge of the second sheet, so that the edge of the first sheet is separated from the edge of the second sheet.

5. The body fluid collection device according to claim 1, wherein the first sheet, the second sheet, and the third sheet are each a sheet which is flat, arc-surface, or partly flat and partly arc-surface in natural state, and is made of an elastic or non-elastic material.

6. The body fluid collection device according to claim 1, wherein a spacer is disposed between the fourth surface of the second sheet and the fifth surface of the third sheet, so that the fourth surface of the second sheet and the fifth surface of the third sheet do not come into full contact with each other and do not form a closed space inside the bag body, and the spacer has a three-dimensional structure and comprises at least one component selected from the group consisting of a bubble wrap, a corrugated board, and one or more tubular elements.

7. The body fluid collection device according to claim 1, wherein the fourth surface of the second sheet is partially connected to the fifth surface of the third sheet, dividing the bag body into two spaces which are in communication with each other through a passage, a spacer is further disposed in the passage so that the two spaces of the bag body are in communication with each other through the spacer, and the spacer is a unidirectional element having a one-way flow guiding function and comprises at least one component selected from the group consisting of a one-way valve and a flow meter.

8. The body fluid collection device according to claim 1, wherein the second sheet and the third sheet are each a rounded rectangle having a long symmetry axis and a short symmetry axis, and the opening is provided at a middle point of the long symmetry axis or adjacent to an end of the long symmetry axis.

9. The body fluid collection device according to claim 8, wherein a ratio of the long symmetry axis to the short symmetry axis is greater than 2:1.

10. The body fluid collection device according to claim 1, wherein the first sheet is made of a microporous film, having an air permeability which is a moisture vapor transmission rate (MVTR) of greater than or equal to 500 g/(m$^2$·24 h), and having a water permeability of greater than or equal to 1000 g/(m$^2$·24 h) after gluing.

11. The body fluid collection device according to claim 1, wherein the first sheet is provided with at least one arc-shaped notch or is provided with a petal-shaped edge so as to well fit a non-planar surface.

12. The body fluid collection device according to claim 1, wherein the body fluid collection device further comprises at least one drainage tube, which is connected to the second sheet or the third sheet of the bag body, so that inside of the bag body is in communication with outside of the bag body through the drainage tube, and the drainage tube is configured in such a manner that:
the second closed strip-shaped region has an open part, and the drainage tube passes through the open part and is then sandwiched between the second sheet and the third sheet; or
the second sheet or the third sheet is provided with at least one flow guiding opening, and the drainage tube is disposed corresponding to the flow guiding opening, wherein one end of the drainage tube is provided with a brim portion, which is substantially perpendicular to an axial direction of the drainage tube, surrounds the drainage tube, and is connected to the third surface of the second sheet or the sixth surface of the third sheet.

13. The body fluid collection device according to claim 12, wherein the drainage tube comprises a cap, and the drainage tube is configured to be opened or closed in one of the following manners:
the cap and the drainage tube are threadedly engaged with each other;
one of the cap and the drainage tube is provided with a flange and the other is provided with a concave edge, so that the two are engaged with each other; and
one of the cap and the drainage tube is plugged into the other by means of material elasticity and friction.

14. A body fluid collection device for contraception, comprising:
a first sheet, provided with a first opening and comprising a first surface and a second surface;
an adhesive layer, disposed on the first surface of the first sheet;
a second sheet, provided with a second opening and comprising a third surface and a fourth surface, the third surface being connected to the second surface of the first sheet with a first closed strip-shaped region, an outer edge of the first closed strip-shaped region being located between an edge of the first sheet and the first opening;

and a third sheet, provided with a fifth surface and a sixth surface, the fifth surface being connected to the fourth surface of the second sheet with a second closed strip-shaped region, so that an edge of the third sheet is connected to an edge of the second sheet in an enclosed manner so as to form a bag body having an opening;

wherein the first sheet has a thickness of less than 0.1 mm;

wherein the second sheet or the third sheet has a perimeter of less than 180 mm and a thickness of less than 0.1 mm, and the bag body has a volume of less than 20 mL; and wherein the body fluid collection device further comprises a structure support unit, extending along the edge of the first sheet.

\* \* \* \* \*